(12) United States Patent
Ornatsky

(10) Patent No.: US 9,284,597 B2
(45) Date of Patent: Mar. 15, 2016

(54) METHODS TO ASSAY KINASE ACTIVITY

(71) Applicant: Fluidigm Canada Inc., Markham (CA)

(72) Inventor: Olga Ornatsky, Richmond Hill (CA)

(73) Assignee: Fluidigm Canada Inc., Markham (CA)

( * ) Notice: Subject to any disclaimer, the term of this patent is extended or adjusted under 35 U.S.C. 154(b) by 0 days.

(21) Appl. No.: 14/327,948

(22) Filed: Jul. 10, 2014

(65) Prior Publication Data
US 2014/0323339 A1 Oct. 30, 2014

Related U.S. Application Data

(62) Division of application No. 13/683,002, filed on Nov. 21, 2012, now Pat. No. 8,790,886, which is a division of application No. 13/313,427, filed on Dec. 7, 2011, now Pat. No. 8,338,126, which is a division of application No. 11/674,455, filed on Feb. 13, 2007, now Pat. No. 8,093,014.

(60) Provisional application No. 60/772,584, filed on Feb. 13, 2006.

(51) Int. Cl.
*C12Q 1/48* (2006.01)
*C12Q 1/42* (2006.01)
*G01N 33/569* (2006.01)
*G01N 33/58* (2006.01)
*G01N 33/68* (2006.01)

(52) U.S. Cl.
CPC *C12Q 1/42* (2013.01); *C12Q 1/485* (2013.01); *G01N 33/569* (2013.01); *G01N 33/58* (2013.01); *G01N 33/6842* (2013.01); *G01N 33/6848* (2013.01); *G01N 2458/15* (2013.01); *Y10S 435/975* (2013.01)

(58) Field of Classification Search
None
See application file for complete search history.

(56) References Cited

U.S. PATENT DOCUMENTS

| 6,031,074 | A | 2/2000 | Saxinger | |
| 6,599,711 | B2 | 7/2003 | Crouch et al. | |
| 6,846,645 | B2 | 1/2005 | Xue et al. | |
| 8,093,014 | B2* | 1/2012 | Ornatsky | 435/21 |
| 8,338,126 | B2* | 12/2012 | Ornatsky | 435/21 |
| 8,790,886 | B2* | 7/2014 | Ornatsky | 435/15 |
| 2005/0227290 | A1 | 10/2005 | Lippard et al. | |
| 2007/0054304 | A1 | 3/2007 | Agnew et al. | |
| 2007/0238143 | A1 | 10/2007 | Xia et al. | |
| 2008/0108128 | A1* | 5/2008 | Eidne et al. | 435/235.1 |
| 2012/0077714 | A1 | 3/2012 | Nolan et al. | |
| 2012/0164632 | A1 | 6/2012 | Ornatsky et al. | |
| 2012/0270251 | A1 | 10/2012 | Roth et al. | |

FOREIGN PATENT DOCUMENTS

| EP | 1662258 | * | 5/2006 |
| WO | 02/054075 | A1 | 7/2002 |
| WO | 2004/059291 | A2 | 7/2004 |
| WO | 2005/003767 | A2 | 1/2005 |
| WO | 2005/047901 | A2 | 5/2005 |
| WO | 2005/093784 | A1 | 10/2005 |
| WO | 2005/123959 | A2 | 12/2005 |
| WO | 2007/093049 | A1 | 8/2007 |

OTHER PUBLICATIONS

Bandura, D. et al. "Characterization of Phosphorus Content of Biological Samples by ICP-DRC-MS," Jan. 2004, J Analytical Atomic Spectrometry, vol. 19, No. 1, pp. 96-100.
Baranov, et al. "A Sensitive and Quantitative Element-Tagged Immunoassay with ICPMS Detection," 2002, Analyt Chem, VO. 74, No. 7, pp. 1629-1636.
Cao, Y.W. et al. "DNA-Modified Core-Shell Ag/AU Nanoparticles," 2001, J Am Chem Soc, vol. 123, No. 32, pp. 7961-7962.
Chen, C. et al. "Biosensors of Protein Kinase Action: From in vitro Assays to Living Cells," Mar. 11, 2004, vol. 1697, No. 1-2, pp. 39-51.
Cooper et al. "The When and How of Src Regulation," 1993, Cell, vol. 73, pp. 1051-1054.
Gaudet, E. et al. "A Homogeneous Fluorescence Polarization Assay Adaptable for a Range of Protein Serine/Threonine and Tryosine Kinases," Apr. 2003, J Bimolecular Screening, vol. 8, No. 2, pp. 164-175.
Hackel et al. "Epidermal Growth Factor Receptors: Critical Mediators of Multiple Receptor Pathways," 1999, Current Opinion in Cell Biology, vol. 11, pp. 184-189.
International Preliminary Report on Patentability issued Aug. 19, 2008, for PCT Patent Application No. PCT/CA2007/000222.
International Search Report issued on May 23, 2007 for PCT Patent Application No. PCT/CA2007/000222.
Larsen, M. et la. "Highly Selective Enrichment of Phosphorylated Peptides from Peptide Mixtures Using Titanium Dioxide Microccoumns," Jul. 2005, Molecular & Cellular Proteomics, vol. 7, No. 7, pp. 873-886.
Mandell, J.W. "Phosphorylation State-Specific Antibodies Applications in Investigative and Diagnostic Pathology," 2003, Am J Path, vol. 163, No. 5, pp. 1687-1698.
Merocki, A. et al. "Toward an ICPMKS-Linked DNA Assay Based on Gold Nanoparticles Immunoconnected Through Peptide Sequences," 2005, Anal Chem, vol. 77, pp. 6500-6503.
Meyer et al. "Molecular-Level Electron Transfer and Excited State Assemblies on Surfaces of Metal Oxides and Glass," 1994, Inorganic Chemistry, vol. 33, pp. 3952-3964.

(Continued)

Primary Examiner — Ralph Gitomer
(74) Attorney, Agent, or Firm — Kilpatrick Townsend & Stockton LLP

(57) ABSTRACT

Methods and kits for enzymes involved in post-translational modifications are provided. The methods employ elemental analysis, including ICP-MS. The methods allow for the convenient and accurate analysis of post-translation modifications of substrates by enzymes involved in post-translational modifications, including kinase and phosphatase enzymes.

7 Claims, 8 Drawing Sheets

(56) References Cited

OTHER PUBLICATIONS

Ornatsky, O. et al. "Messenger RNA Detection in Leukemia Cell Lines by Novel Metal-Tagged in situ Hybridization Using Using Inductively Coupled Plasma Mass Spectrometry," 2006, Translational Oncogenomics, pp. 1-9.

Ornatsky, O. et al. "Multiple Cellular Antigen Detection by ICP-MS," 2006, J Immunol Meth, vol. 308, pp. 68-76.

Quinn, Z.A. et al. "Simultaneous Determination of Proteins Using an Element-Tagged Immunoassay Coupled with ICP-MS Detection," 2002, JAAS, vol. 17, pp. 892-896.

Schlosser et al. "Mapping of Phosphorylation Sites by a Multi-Protease Approach with Specific Phosphopeptide Enrichment and NanoLC-MS/MS Analysis," 2005, Anal Chem, vol. 77, pp. 5243-5250.

Thomas, R.N. et al. "Nanosphere-Antibody Conjugates with Releasable Fluorescent Probes," 2001, Fresenius J Anal Chem, vol. 369, pp. 477-482.

Written Opinion of the International Searching Authority dated May 14, 2007 for PCT Patent Application No. PCT/CA2007/000222.

* cited by examiner

SEQUENCE LISTING

<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)..(1)
<223> OTHER INFORMATION: biotinylated Pro

<400> SEQUENCE: 1

```
Pro Arg Pro Ala Ala Thr Phe
1               5

<210> SEQ ID NO 2
<211> LENGTH: 26
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)..(1)
<223> OTHER INFORMATION: biotinylated Tyr
<220> FEATURE:
<221> NAME/KEY: MOD_RES
<222> LOCATION: (21)..(21)
<223> OTHER INFORMATION: PHOSPHORYLATION

<400> SEQUENCE: 2

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 3
<211> LENGTH: 38
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)..(1)
<223> OTHER INFORMATION: biotinylated Lys
<220> FEATURE:
<221> NAME/KEY: MOD_RES
<222> LOCATION: (4)..(4)
<223> OTHER INFORMATION: Xaa is Orn

<400> SEQUENCE: 3

Lys Thr Phe Xaa Gly Thr Pro Glu Tyr Leu Ala Pro Glu Val Arg Arg
1               5                   10                  15

Glu Pro Arg Ile Leu Ser Glu Glu Gln Glu Met Phe Arg Asp Phe
            20                  25                  30

Asp Tyr Ile Ala Asp Trp
        35

<210> SEQ ID NO 4
<211> LENGTH: 11
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)..(1)
<223> OTHER INFORMATION: biotinylated Gln

<400> SEQUENCE: 4

Gln Lys Arg Pro Ser Gln Arg Ser Lys Tyr Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic peptide construct
<220> FEATURE:
```

```
<221> NAME/KEY: MOD_RES
<222> LOCATION: (5)..(5)
<223> OTHER INFORMATION: phosphorylated Tyr

<400> SEQUENCE: 5

Asp Ala Asp Glu Tyr Leu Ile Pro Gln Gln Gly
1               5                   10
```

METHODS TO ASSAY KINASE ACTIVITY

CROSS REFERENCE TO RELATED APPLICATIONS

This application is a divisional of U.S. patent application Ser. No. 13/683,002, filed Nov. 21, 2012, now issued as U.S. Pat. No. 8,790,886, issued Jul. 29, 2014, which is a divisional of U.S. patent application Ser. No. 13/313,427, filed Dec. 7, 2011, now issued as U.S. Pat. No. 8,338,126 B2, issued Dec. 25, 2012, which is a divisional of U.S. patent application Ser. No. 11/674,455, filed Feb. 13, 2007, now issued as U.S. Pat. No. 8,093,014 B2, issued Jan. 10, 2012, which claims the benefit of U.S. Provisional Patent Application Ser. No. 60/772,584, filed Feb. 13, 2006.

REFERENCE TO A SEQUENCE LISTING

The Sequence Listing written in file SequenceListing_085665-0914473.txt, created on Dec. 28, 2015, 2,301 bytes, machine format IBM-PC, MS-Windows operating system, is hereby incorporated by reference in its entirety for all purposes.

COPYRIGHT AND LEGAL NOTICES

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

FIELD OF THE INVENTION

This invention pertains to the determination of post-translational modification of proteins such as phosphorylation and dephosphorylation, including methods and kits, employing elemental analysis.

BACKGROUND OF THE INVENTION

The methods described facilitate high-throughput assays through multiplexing assays that until now have largely been performed individually. The principal, but not exclusive, target of the method is to provide for the evaluation of agonists and antagonists to phosphorylation (kinase) and dephosphorylation (phosphatase), as these are targets for pharmaceutical drug discovery applications.

Overall there are no less than 20 platform technologies available (for example, Radioactivity, Fluorescence Polarization, Time Resolved Fluorescence, Fluorescence Resonance Energy Transfer[1], etc.), however most display important limitations for the development of a coherent screening-profiling platform. Well known drawbacks include those related to heterogeneous assay systems, limitations in ATP concentration, compound interferences and limitations of substrate size and charge. As well these methods have low level of sensitivity and are difficult to multiplex[2], i.e. assay dozens of different kinases/phosphatases simultaneously. Thus there are many needs unfulfilled by the prior art, including but not limited to a need for a sensitive, robust and quantitative assay for protein post-translational modification. Further, there is a need for a multiplexed enzymatic assay that enables high throughput operation.

Among the many advantages offered by the applicant's teaching are the following: I. The assay can be applied to any type of protein kinase; II. The assay can be applied to any type of protein phosphatase; III. The assay does not exclusively rely on the use of antibodies (although some embodiments might include antibodies); IV. The methods can be used to detect and study protein kinase antagonists and agonists; V. The methods can be used to study protein kinase signal transduction cascades; VI. The methods can be used with a number of different protein kinase buffers; VII. The assay can be supplied as a kit; VIII. The assay can be used to measure activity of multiple kinases/phosphatases in cell free systems; IX. The assay can be used to determine activity of multiple kinases/phosphatases in cellular lysates; X. The assay can be used to determine various endogenous and transfected kinase activities within intact cells.

Post-translational modifications of proteins are carried out by enzymes within living cells. Known post-translational modifications include protein phosphorylation and dephosphorylation as well as methylation, prenelation, sulfation, and ubiquitination. The presence or absence of the phosphate group on proteins, especially enzymes, is known to play a regulatory role in many biochemical pathways and signal transduction pathways. Hence together, specialized kinases and phosphatases regulate enzymatic activity.

A kinase function is to transfer phosphate groups (phosphorylatiOn) from high-energy donor molecules, such as ATP, to specific target molecules (substrates). An enzyme that removes phosphate groups from targets is known as a phosphatase. The largest group of kinases are protein kinases, which act on and modify the activity of specific proteins. Various other kinases act on small molecules (lipids, carbohydrates, aminio acids, nucleotides and more) often named after their substrates and include: Adenylate kinase, Creatine kinase, Pyruvate kinase, Hexokinase, Nucleotide diphosphate kinase, Thymidine kinase.

Protein kinases catalyze the transfer of phosphate from adenosine triphosphate (ATP) to the targeted peptide or protein substrate at a serine, threonine, or tyrosine residue. Protein kinases are distinguished by their ability to phosphorylate substrates on discrete sequences. Commercially available kinases can be in the active form (phosphorylated by supplier) or in the inactive form and require phosphorylation by another kinase.

A protein phosphatase hydrolyses phosphoric acid monoesters at phosphoserine, phosphothreonine, or phosphotyrosine residue into a phosphate ion and a protein or peptide molecule with a free hydroxy group. This action is directly opposite to that of the protein kinase. Examples include: the protein tyrosine phosphatases, which hydrolyse phospho-tyrosine residues, alkaline phosphatase, the serine/threonine phosphatases and inositol monophosphatase.

DEFINITIONS

"Protein kinase or phosphatase" as used in the invention may be natural, recombinant or chemically synthesized. If either natural or recombinant, it may be substantially pure (i.e., present in a population of molecules in which it is at least 50% homogeneous), partially purified (i.e., represented by at least 1% of the molecules present in a fraction of a cellular lysate) or may be present in a crude biological sample.

"Enzyme (kinase, phosphatase) assays" may target principally one of three quantities: concentration (of either the enzyme or the substrate on which it works); activity of the enzyme on the substrate or substrates; and specificity of the enzymatic activity for a given substrate or suite of substrates.

The assay is of value in the determination of the impact of agonists and antagonists on the activity and specificity of the enzymatic action. Examples of the type of information that may be obtained from such assays include: I. The specificity of action on a suite of substrates can be determined if the enzyme is known to be present; II. The activity of the enzyme towards each of a suite of substrates can be determined if the concentration of the enzyme and the time of interaction is known; III. The presence of an enzyme can be determined if action on a substrate is detected; IV. The concentration of the enzyme can be determined if the concentration of the substrate and the activity of the enzyme for that substrate and the time of interaction is known.

"Specific kinase assay" refers to an enzyme assay specific for individual kinases in the presence or absence of other phosphatases and kinases.

"Specific phosphatase assay" refers to an enzyme assay specific for individual phosphatase in the presence or absence of other phosphatases and kinases.

"Non-phosphorylated substrate" is biological material that may be phosphorylated by a protein kinase. The substrate which is targeted by kinases may be a structural protein or another enzyme which is a functional protein or a peptide or a lipid. For example, protein substrates that are typically used in an assay for specific kinase activity include milk casein; histones, isolated from calves; phosphovitin, isolated from egg yolks; and myelin basic proteins, isolated from bovine spinal cords. Production of peptides may be achieved by enzymatic digestion of full length proteins, chemical synthesis[3] or expression of a recombinant peptide. Peptide substrates may contain from about 6 to about 50 amino acids.

"Element tag" or "tag" is a chemical moiety which includes any elemental atom or multitude of elemental atoms having one or many isotopes attached to a supporting molecular structure. The element tag can also comprise the means of attaching the tag to a substrate. Different element tags may be distinguished on the basis of the elemental composition of the tags. A tag may contain many copies of a given isotope and may have a reproducible copy number of each isotope in each tag. An element tag may be distinguishable from a multitude of other element tags in the same sample because its elemental or isotopic composition is different from that of other tags. For example, the element tag could be a metal-chelate polymer with an attachment group. The element can be selected from a group consisting of the noble metals, lanthanides, rare earth elements, transition elements, gold, silver, platinum, rhodium, iridium and palladium. The element can be an isotope. The element can include more than one atom of an isotope. For example, an elemental tag can be a metal-chelate polymer with an attachment group. As is known to those skilled in the art, an element tag can be an atomic part of chemical moiety, such as for example Ti in a titanium dioxide particle.

A "support" is a surface which has been functionalized by, for example, pyrrole-2,5-dione (rnaleimido), sulfonic acid anion, or p-(chloromethyl) styrene. A support, for example, may be but is not limited to, a synthetic membrane, bead (polystyrene, agarose, silica, etc), planar surface in plastic microwells, glass slides, reaction tubes, etc. as is known to those skilled in the art.

Element labeled bead" is a type of support bead (polystyrene, agarose, silica, etc) which functionally incorporates or is imbibed with an element or multitude of elements with one or many isotopes. As is known to those skilled in the art, an element can be an atomic part of chemical moiety, such as for example Ti in titanium dioxide.

"Uniquely labeled bead" refers to a physical entity that includes a multitude of atoms of one or more isotopes of one or more elements imbibed in a bead such that one type of said bead labeled with one or more isotopes or elements is distinguishable from other types of said beads labeled with distinguishable elements or isotopes by elemental analysis. Each uniquely labeled bead can bear a multitude of substrates specific for a given enzyme.

A "substrate labeled with an element" tag is a substrate which has included an element tag which allows the substrate to be determined by elemental analysis.

A "substrate labeled with a unique element tag" is a substrate labeled with an element tag that is distinguishable from a multitude of other element tags in the same sample and whose presence is indicative of the substrate specific to that tag.

A "free phosphorylated substrate" is a substrate that is phosphorylated after synthesis or synthesized using phosphorylated amino acids. Phosphorylamino acids for incorporation into chemically synthesized peptides may be obtained from numerous commercial sources as is known to those skilled in the art.

A "phosphorylated substrate" is distinguished from a "non-phosphorylated substrate" primarily by the presence of a phosphate group.

"Metal ion coordination complex" is an association of a central metal ion and surrounding ligands, in particular transition metal, rare earth and other metal (Ga(III), Fe(III), Al(III), Sc(lll), Lu(lll), Th(III), Zr(IV), complexes, for example, but not limited to, of iminodiacetic acid (IDA) or nitrilotriacetic acid (NTA). Metal oxide forms (such as TiO2, ZrO2, indium tin oxide) are metal compounds with coordinating properties for phosphate ions relevant to the present invention. These have been widely adopted in biology, and are gaining increasing use in biotechnology, particularly in the protein purification technique known as Immobilised Metal-ion Affinity Chromatography (IMAC).

Reactions are allowed to proceed for various durations and at different temperatures. The reaction conditions vary depending on the specific kinase/phosphatase, as is known to those skilled in the art. For many mammalian kinases, the reaction is carried out at room (25° C.) or elevated temperatures, usually in the range of 20° C. to 40° C. For high-throughput applications, reaction time is minimized, and is usually from 10 minutes to 4 hours, more usually about 10 minutes to 1 hour.

"Elemental analysis" is a process where a sample is analyzed for its elemental composition and sometimes isotopic composition. Elemental analysis can be accomplished by a number of methods, including but not limited to: I. Optical atomic spectroscopy, such as flame atomic absorption, graphite furnace atomic absorption, and inductively coupled plasma atomic emission, which probe the outer electronic structure of atoms; II. Mass spectrometric atomic spectroscopy, such as inductively coupled mass spectrometry, which probes the mass of atoms; III. X-ray fluorescence, particle induced x-ray emission, x-ray photoelectron spectroscopy, and Auger electron spectroscopy which probes the inner electronic structure of atoms.

"Elemental analyzer" is an instrument for the quantitation of atomic composition of a sample employing one of the methods of elemental analysis.

"Particle elemental analysis" is a process where an analyzed sample, composed of particles dispersed in a liquid (beads in buffer, for example), is interrogated in such manner that the atomic composition is recorded for individual particles (bead-by-bead, for example).

"Solution (volume) elemental analysis" is a process where an analyzed sample is interrogated in such manner that the atomic composition is averaged over the entire volume of the sample.

"Transition element" means any element having the following atomic numbers, 21-29, 39-47, 57-79 and 89. Transition elements include the rare earth elements, lanthanides and noble metals (Cotton and Wilkinson, 1972).

"Affinity product" or "affinity reagent" refers to biological molecules (for example, but not limited to antibody, aptamer, lectin, sequence-specific binding peptide, etc) which are known to form highly specific non-covalent bonds with respective target molecules (peptides, antigens, small molecules, etc). Affinity reagent labeled with a unique element tag is an affinity product labeled with an element tag that is unique and distinguishable from a multitude of other element tags in the same sample.

Kinase reaction buffer—There are a number of examples of reaction buffers formulated for specific kinases in the literature. The reaction generally requires the presence of an effective amount of a nucleoside triphosphate, such as ATP, usually at a concentration in the range of about 0.01-20 mM. As is known to those skilled in the art, the buffer may contain substances such as HEPES or Tris-HCl, at a concentration in the range of about 1-50 mM, at a pH of about 5-9. Individual enzymes may generally be present in an amount in the range of 1 pg-5 ng/μl. Cations such as Mg, Mn and Ca, at concentrations 0.1-5 mM may be employed. Other additives may include DTT at a concentration in the range of 0.1-2 mM. In some instances sodium ortho-vanadate may be used at a concentration of about 0.5-2 mM to inhibit contaminating phosphatases. Also, an inert protein may be included, such as ovalbumin, serum albumin, etc., at 0.1-5 mg/mi, to prevent non-specific binding and inactivation of low concentration assay components, especially to prevent enzyme binding to the surface. For some protein kinases, other cofactors may be required such as phospholipids, calmodulin, cAMP, phosphotidyiserine, and diolein, as is known to those skilled in the art.

Phosphatase reaction buffer is a solution of Tris-HCl, at a concentration in the range of about 50-100 mM, at a pH of about 8-9.5, and 100 mM NaCl. Individual enzymes may generally be present in an amount in the range of about 1 pg-5 ng/pl. Cations such as Mg, Mn and Ca, at concentrations 1-5 mM may be employed. Other additives may include DTT at a concentration in the range of 0.1-2 mM.

Methods of separation may include washing of the support by addition of washing buffer (may consist of a solution of 100-150 mM NaCl, 50-100 mM Tris-HCl pH 7) and aspiration of said wash buffer from container (well of a multiwell plate, microtube, etc). If assay if performed with a bead support or with element labeled beads, the method of separation may include low speed centrifugation (300-9,300×g), with or without Molecular Weight Cut Off (MWCO) filtration devices.

Elution (of an element tag and/or a metal coordination complex) into solution means (preferably quantitative) solubilization of the elements comprising the tag and or metal atom(s) of the metal coordination complex, in a form to allow solution elemental analysis. Elution may include conventional elution buffers and solvents that maintain the molecular constructs intact, or may involve acid degradation or other means to convert the elements or metals of interest into solution or slurry as is known to those skilled in the art.

SUMMARY OF THE INVENTION

These and other features of the applicant's teachings are set forth herein. An aspect of the applicant's teachings is to provide a method for a kinase assay, comprising: incubating ATP, at least one kinase, and a free non-phosphorylated substrate labeled with an element tag, with a support having attached thereto metal ion coordination complexes under conditions to enable the kinase to phosphorylate the substrate; separating free non-phosphorylated substrate from bound phosphorylated substrate labeled with an element tag to the support; eluting the element tag associated with the resultant phosphorylated substrate into a solution; and performing solution elemental analysis of said solution.

Another aspect of the applicant's teachings is to provide a method for a phosphatase assay, comprising: incubating free phosphorylated substrate labeled with an element tag with a support having attached thereto metal ion coordination complexes; separating free phosphorylated substrate from bound phosphorylated substrate labeled with an element tag attached to the metal ion coordination complexes attached to the support; incubating ADP and at least one phosphatase with the bound phosphorylated substrate labeled with an element tag attached to the metal ion coordination complexes attached to the support under conditions to enable the phosphatase to dephosphorylate the substrate; separating free non-phosphorylated substrate labeled with an element tag from bound phosphorylated substrate attached to the metal ion coordination complexes attached to the support; and measuring the tag element in a solution of the free non-phosphorylated substrate.

Another aspect of the applicant's teachings is to provide a method for a phosphatase assay, comprising: incubating, in a multitude of solutions, each solution comprising a different free phosphorylated substrate labeled with an element tag, which can optionally be the same element tag for all substrates, a plurality of element labeled supports having attached thereto a metal ion coordination complex, in such manner that each type of phosphorylated substrate labeled with an element tag, which can optionally be the same element tag for all substrates, is attached to a single type of element labeled support; separating free phosphorylated substrate from the bound substrate attached to the metal ion coordination complex attached to the multitude of element labeled supports in the multitude of separate solutions; incubating the multitude of element labeled supports having attached thereto the multitude of phosphorylated substrates labeled with an element tag, which can optionally be the same element tag for all substrates, through attachment to the metal ion coordination complex that is attached to the supports in a single solution with ADP and at least one phosphatase in conditions that enable the phosphatase to dephosphorylate the phosphorylated substrates; separating free non-phosphorylated substrate from bound phosphorylated substrate labeled with an element tag, which can optionally be the same element tag for all substrates, attached to the metal ion coordination complex attached to said multitude of element labeled supports; and performing particle elemental analysis of bound phosphorylated substrate labeled with an element tag, which can optionally be the same element tag for all substrates, attached to the metal ion coordination complex attached to the multitude of element labeled supports.

Another aspect of the applicant's teachings is to provide a method for a kinase assay, comprising: incubating ATP, at least one kinase, and a free metal ion coordination complex, with an immobilized non-phosphorylated substrate under conditions which enable the kinase to phosphorylate the substrate; separating immobilized phosphorylated substrate attached to the metal ion coordination complex from the free ion coordination complex and the immobilized non-phosphorylated substrate; eluting the metal ion coordination complex attached to the immobilized phosphorylated substrate into a solution; and measuring the solution by elemental analysis.

Another aspect of the applicant's teachings is to provide a method for a kinase assay, comprising: incubating ATP, at least one kinase, a free metal ion coordination complex, and a multitude of non-phosphorylated substrates immobilized on element labeled supports in such manner that a single type of non-phosphorylated substrate is attached to a single type of element labeled support, in conditions to enable the kinase to phosphorylate the substrates; separating the multitude of phosphorylated substrates immobilized on element labeled supports having attached metal ion coordination complex from the free metal ion coordination complexes and the multitude of immobilized non-phosphorylated substrates; and measuring the multitude of phosphorylated substrate immobilized on element labeled supports having attached metal ion coordination complex by elemental analysis.

Another aspect of the applicant's teachings is to provide a method for a kinase assay, comprising: introducing a multitude of non-phosphorylated substrates with element tags into live cells; incubating the cells having the introduced nonphosphorylated substrates with an agonist or an antagonist of kinase activity; fixing and permeabilizing the cells; incubating the cells with element-labeled antibodies directed against phosphospecific kinase substrates; separating the cells from unbound antibodies; and measuring the phosphorylated substrates with element tags and attached element-labeled antibodies by elemental analysis.

Another aspect of the applicant's teachings is to provide a method for a phosphatase assay, comprising: incubating ADP and at least one phosphatase, with an immobilized phosphorylated substrate with attached metal ion coordination complexes in conditions that enable the phosphatase to dephosphorylate the substrate; separating the free metal ion coordination complex from the immobilized non-phosphorylated substrate and the immobilized phosphorylated substrate with attached metal ion coordination complex; eluting the metal ion coordination complex into a solution; and measuring the solution by elemental analysis.

Another aspect of the applicant's teachings is to provide a method for phosphatase assay, comprising: incubating ADP, at least one phosphatase, and a multitude of phosphorylated substrates with attached metal ion coordination complex immobilized to element labeled supports in such manner that a single type of phosphorylated substrate is attached to a single type of element labeled support in conditions that enable the phosphatase to dephosphorylate the phosphorylated substrates; separating the free metal ion coordination complex from the multitude of non-phosphorylated substrates immobilized to element labeled supports and the multitude of immobilized phosphorylated substrate; and measuring the metal ion coordination complex attached to the multitude of phosphorylated substrate immobilized to uniquely labeled supports by elemental analysis.

Another aspect of the applicant's teachings is to provide a kit for the detection and measurement of elements in a sample, where the measured elements include an element tag attached to a non-phosphorylated substrate and a metal ion coordination complex, comprising: an element tag for directly tagging nonphosphorylated substrate; non-phosphorylated substrate; a solid support; a metal ion coordination complex; and optionally, kinase; kinase buffer; and ATP. The kit can urther comprise instructions for i) directly tagging the non-phosphorylated substrate with an element tag; ii) incubating kinase with element labeled non-phosphorylated substrate in kinase buffer, iii) attaching metal ion coordination complex to the support; iv) incubating the kinase with element labeled non-phosphorylated substrate in kinase buffer with the support having attached metal ion coordination complex; v) separating bound substrate from unbound substrate; vi) eluting the bound substrate, and vii) detecting and measuring the bound substrate by elemental analysis.

Another aspect of the applicant's teachings is to provide a kit for the detection and measurement of elements in a sample, where the measured elements include element labels of uniquely labeled supports and an element of a metal ion coordination complex, comprising: a multitude of non-phosphorylated substrates; uniquely labeled supports; metal ion coordination complex; and optionally, kinase; kinase buffer; and ATP. The kit can further comprise instructions for I) immobilizing the non-phosphorylated substrates on element labeled supports in separate solutions; ii) incubating kinase in kinase buffer with the multitude of non-phosphorylated substrates immobilized on uniquely labeled supports, iii) incubating the metal ion coordination complex in the kinase buffer with the kinase and the multitude of non-phosphorylated substrates immobilized on uniquely labeled supports, iv) washing and separating bound substrate from unbound substrate; v) measuring the metal ion coordination complex bound to the multitude of phosphorylated substrate immobilized on uniquely labeled supports by elemental analysis.

Another aspect of the applicant's teachings is to provide a kit for the detection and measurement of elements in a sample, where the measured elements include element tags attached to affinity products that recognize phosphorylated substrates, comprising: non-phosphorylated substrate ready to be introduced into a cell; and an element tag for directly tagging an affinity product; and optionally an affinity product. The kit can further comprise instructions for i) introducing the nonphosphorylated substrate into a cell; ii) directly tagging an affinity product that recognizes phosphorylated substrates; iii) fixing and permeabilizing the cells; iv) combining the labeled affinity product with the cells; v) separating bound affinity product from unbound affinity product, and vi) detecting and measuring the amount of the bound affinity product labeled with an element tag by particle elemental analysis.

Another aspect of the applicant's teachings is to provide a kit for the detection and measurement of elements in a sample, where the measured elements include an element tag attached to a phosphorylated substrate and a metal ion coordination complex, comprising: an element tag for directly tagging phosphorylated substrate; phosphorylated substrate; a solid support; metal ion coordination complex; and optionally, phosphatase; phosphatase buffer and ADP. The kit can further comprise instructions for I) direct tagging of the phosphorylated substrate with an element tag; ii) attaching the metal ion coordination complex to the support; iii) incubating the element labeled phosphorylated substrate with the support with attached metal ion coordination complex; iv) separating bound substrate from unbound substrate; v) incubating the phosphatase in phosphatase buffer with the support with the attached metal ion coordination complex; vi) separating bound substrate from unbound substrate; vii) eluting the bound substrate, and viii) measuring the bound substrate by solution elemental analysis.

Another aspect of the applicant's teachings is to provide a kit for the detection and measurement of elements in a sample, where the measured elements include an element tag attached to a phosphorylated substrate, an element of a metal ion coordination complex, and elements of uniquely labeled supports, comprising: an element tag for directly tagging phosphorylated substrate; a multitude of phosphorylated substrates; uniquely labeled supports; metal ion coordination complex; and optionally, phosphatase, phosphatase buffer and ADP. The kit can further comprise instructions for I) direct tagging the phosphorylated substrates with an element tag; ii) attaching a metal ion coordination complex to the uniquely labeled support; iii) adding element labeled phosphorylated substrates to the uniquely labeled support with attached metal ion coordination complex in separate volumes, iv) incubating the substrates; v) washing the supports; vi) combining the multitude of uniquely labeled supports having attached thereto the multitude of resultant phosphorylated substrate labeled with an element tag through coordination to the metal ion coordination complex that is attached to the supports; vii) incubating the phosphatase, the phosphatase buffer and the supports; viii) separating bound substrate from unbound substrate; and ix) measuring the phosphorylated substrate labeled with an element tag coordinated to the metal ion coordination complex attached to said multitude of uniquely labeled supports by particle elemental analysis.

BRIEF DESCRIPTION OF THE DRAWINGS

The invention is illustrated in the figures, which are meant to be exemplary and not limiting.

DESCRIPTION OF THE PREFERRED EMBODIMENTS

Figure 1:
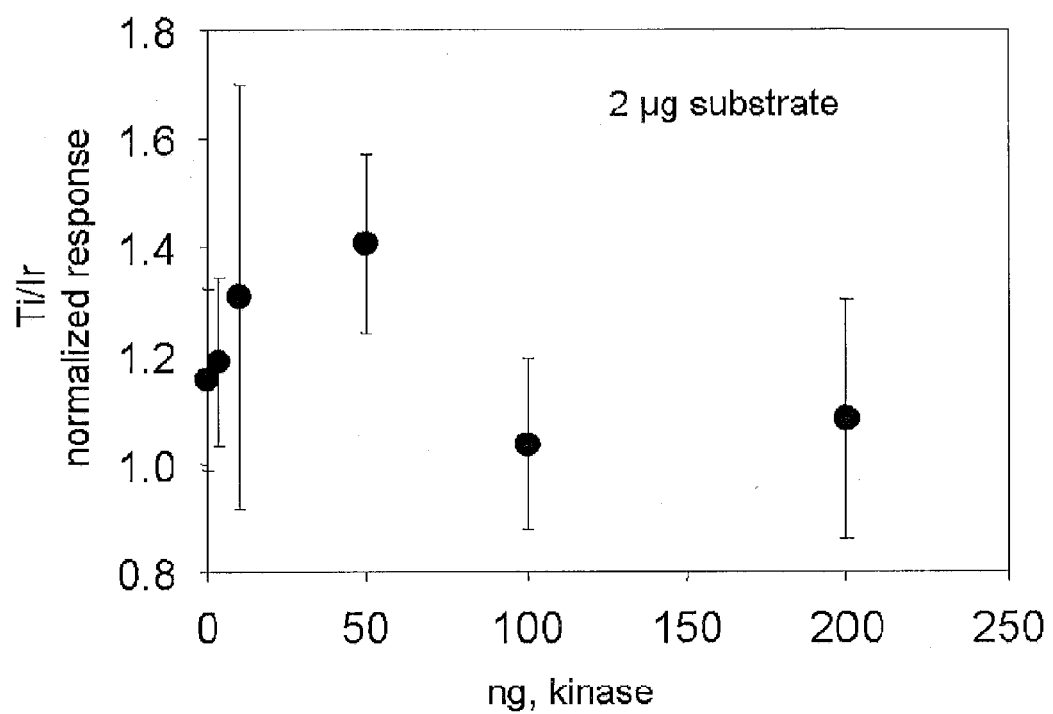
FIG. 1. Dose-dependence curve of EGFR kinase activity. Increasing amounts of EGFR-GST were incubated with 2 ug biotinylated substrate peptide (PTPI B) per reaction per well of 96-well streptavidin coated plate. All reactions were set up in triplicate. Detected signal is presented as normalized response of Ti ions to Ir internal standard.

The present invention comprises use of elemental tags. The choice of the element to be employed in the methods of the applicant's teaching is preferably selected on the basis of its natural abundance in the sample under investigation and whether the element is toxic to the sample under investigation.

Most metals of the transition and rare earth groups are anticipated for use in applicant's teaching. It is wise to choose elements that have low or no cytotoxicity and have a low abundance in growth media and biological samples. For example, vanadium and mercury can be toxic to certain cells, while Fe, Cu and Zn can be present in high concentrations in some cell culture media. On the other hand, Pr, Ho, Tb, La, for example are normally well tolerated by mammalian cells and are not abundant in the environment.

An unusual isotope composition of the tag element can be used in order to distinguish between naturally present elements in the sample and the tag material. It is advantageous if the relative abundance of the tag elements is sufficiently different from the relative abundance of elements in a given sample under analysis. By "sufficiently different" it is meant that under the methods of the present invention it is possible to detect the target elemental tag over the background elements contained in a sample under analysis. Indeed, it is the difference in inter-elemental ratios of the tagging elements and the sample matrix that can be used advantageously to analyze the sample.

It is feasible to select elemental tags, which do not produce interfering signals during analysis (i.e. do not have overlapping signals due to having the same mass). Therefore, two or more analytical determinations can be performed simultaneously in one sample. Moreover, because the elemental tag can be made containing many copies of the same atoms, the measured signal can be greatly amplified.

Aspects of the Applicant's teachings may be further understood in light of the following examples, which should not be construed as limiting the scope of the present teachings in any way.

Epidermal growth factor receptor (EGFR) is a 170 kDa tyrosine kinase. Ligand binding results in receptor dimerization, autophosphorylation on numerous tyrosine residues, activation of downstream signaling and lysosomal degradation.

Phosphorylation of Tyr845 in the kinase domain may stabilize the activation loop, maintaining the enzyme in an active state and provide a binding surface for substrate proteins. c-Src is involved in phosphorylation of Tyr845. Phosphotyrosine 992 is a direct binding site for the PLC-g SH2 domain, resulting in activation of PLC-g mediated downstream signaling. Phosphorylation of Tyr1045 creates a major docking site for c-Cbl. Binding of c-Cbl to the activated EGFR leads to receptor ubiquitination and degradation. Phospho-Tyr1068 of activated EGFR is a direct binding site for Grb2. Phosphotyrosine 1148 and 1173 provide a docking site for SHC. Both sites are involved in the activation of MAP kinase signaling. Phosphorylation of EGFR on serine and threonine residues attenuates EGFR kinase activity. Ser1046/1047 in the carboxy-terminal region of EGFR are sites phosphorylated by CaM kinase II. Mutations of Ser1046/1047 upregulate tyrosine autokinase activity of EGFR. EGFR is highly expressed by A431 epidermoid carcinoma cells (at least 1e6 receptors per cell) and is partly responsible for the active proliferation of these cells.

Experiment 1. In one embodiment, in vitro titration assay for recombinant EGFR kinase and substrate were developed using IC P-MS.

To probe activity of recombinant EGFR, expressed as a GST-kinase fusion protein (EGFR-GST Cell Signaling Tech. #7908), an ICP-MS assay was devised using a biotinylated peptide substrate PTP1B(Tyr66) (Cell Signaling Tech. #1325) and 5% $TiO_2$ particle suspension in water (Sigma #643114). Streptavidin coated 96-well plates (Sigma #M5432) were incubated with 2 ug biotinylated PTB1B in kinase buffer (1× Kinase Buffer: 25 mM Tris-HCl (pH 7.5), 5 mM β-glycerophosphate, 2 mM dithiothreitol (DTT), 0.1 mM Na3VO4, 10 mM MgCl2) and 200 mM ATP, to which various amounts of EGFR-GST were added. All reactions were set up in triplicate. The kinase reaction was stopped after 30 minutes incubation with 50 mM EDTA and all wells were washed 6 times with buffered saline. Thus, only phosphorylated PTP1B(Tyr66) attached to the support through biotin-streptavidin binding remained in the wells. For phosphorylation event detection, a solution of $TiO_2$ diluted a million-fold from the stock 5% in buffered saline was added for binding with phosphate residues on Tyr66. Finally, wells were washed 6 times with buffered saline, and filled with 80 uL concentrated HCl (SeaStar Inc) per well, and an equal volume of 1 ppb 1 r standard was added for further solution analysis by ICP-MS. Results are presented in FIG. 1. The results show that GST-kinase activity follows a dose-dependence curve with the maximum activity at 50 ng of kinase per 2 microg of substrate.

Antagonists and agonists of the enzyme can also be added to the incubation mix. The support can be labeled particles or beads. The active enzyme can be in the form of a cell lysate.

In another embodiment, phosphatase instead of kinase is used as the active enzyme. For example, a solution of free phosphonylated substrate labeled with an element tag can be incubated with a support having attached thereto a metal ion coordination complex. Free phosphorylated substrate can be separated from the bound phosphorylated substrate by methods known to those skilled in the art. ADP and at least one phosphatase can then be incubated with the support under conditions to enable the phosphatase to dephosphonylate the substrate. The free substrate can be removed from the bound substrate and the free substrate can be analyzed by elemental analysis.

Antagonists and agonists of the enzyme can also be added to the incubation mix. The support can be labeled particles or beads. The active enzyme can be in the form of a cell lysate.

Figure 2:
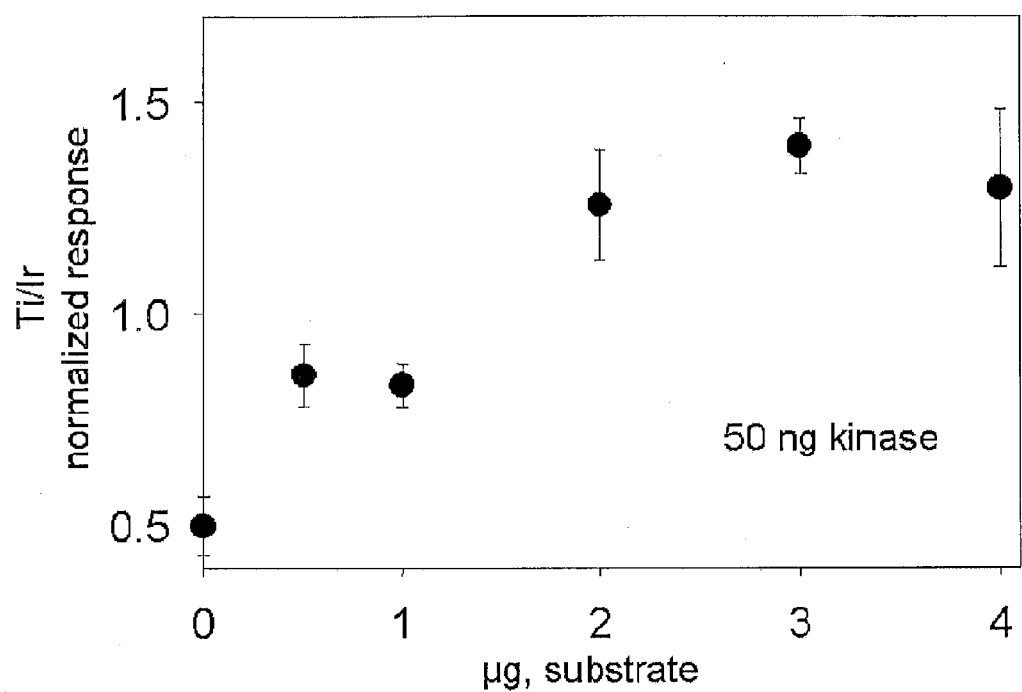
FIG. 2. Peptide concentration dependence of EGFR kinase activity. Increasing amounts of biotinylated substrate peptide (PTP1 B) were incubated with 50 ng of EGFR-GST per reaction per well of 96-well Streptavidin coated plate. All reactions were set up in triplicate. Detected signal is presented as normalized response of Ti ions to Ir internal standard.

Experiment 2. In another embodiment, experiments were designed to probe the peptide concentration dependence of the kinase. The conditions were similar to those describe above except that the amount of GST-EGFR was kept constant at 50 ng per well, while the amounts of PTP1B substrate were varied. Results are shown in FIG. 2. Likewise, the amount of substrate significantly influences the kinase reaction, with 1 microg substrate eliciting a response half of the maximal at 2 microg.

Figure 3:
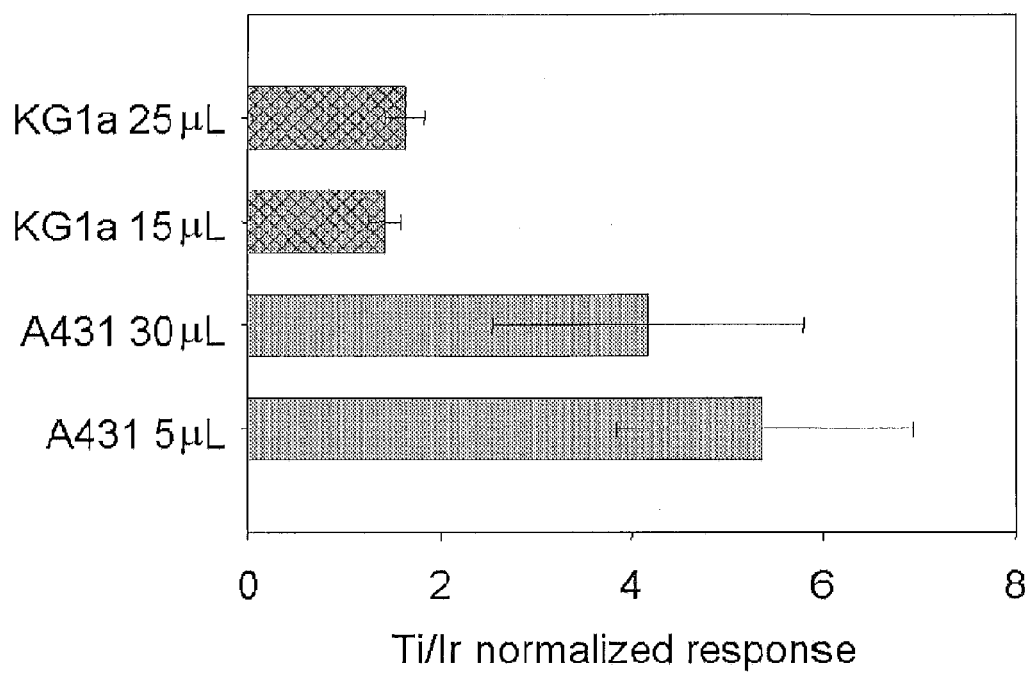
FIG. 3. Intracellular EGFR kinase activity in human cells. Lysates prepared from A431 and KG1-a cells were mixed with PTP1B(Tyr66) substrate linked to agarose beads in the presence of ATP and cations. Washed agarose beads with phosphorylated substrate were incubated with TiO2 particle suspension. Analysis of titanium content in solution was done by ICP-MS. Triplicate samples were set up for analysis.
Figure 4:
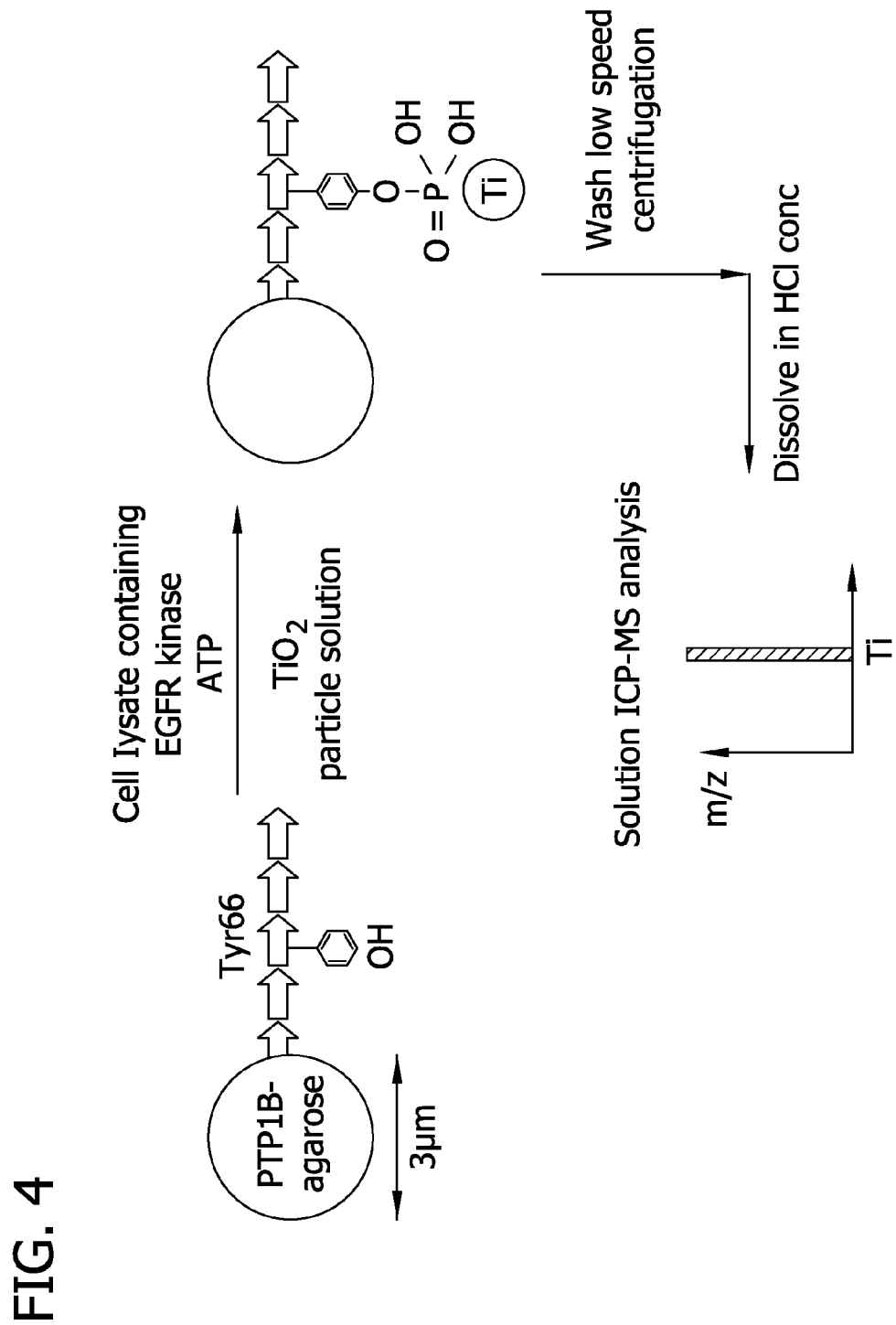
FIG. 4. Schematic representation of solution ICP-MS analysis of kinase activity in cellular lysates, in accordance with the invention.
Figure 5:
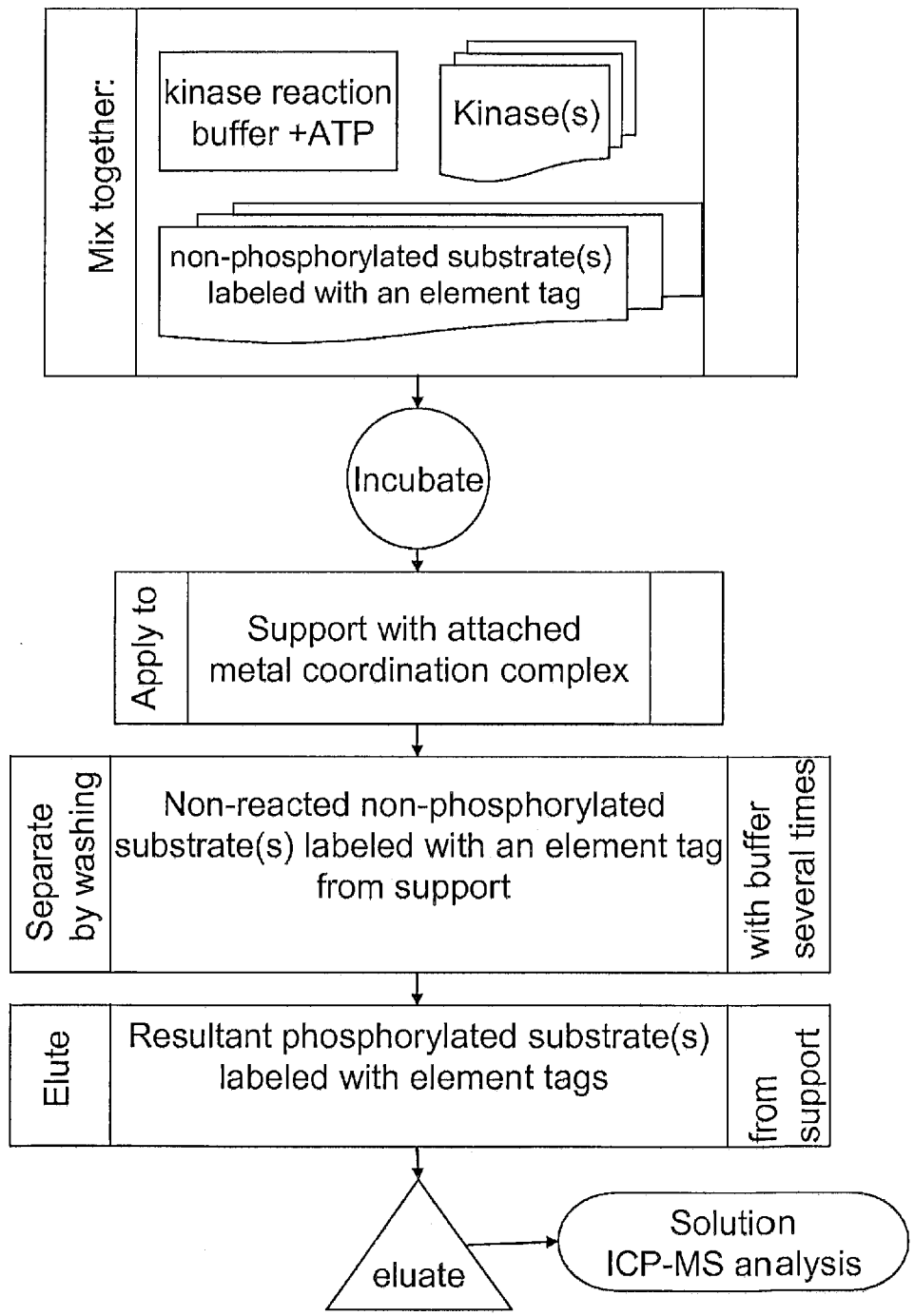
FIG. 5. Flow chart showing method of specific kinase(s) assay, in accordance with the invention.
Figure 7:
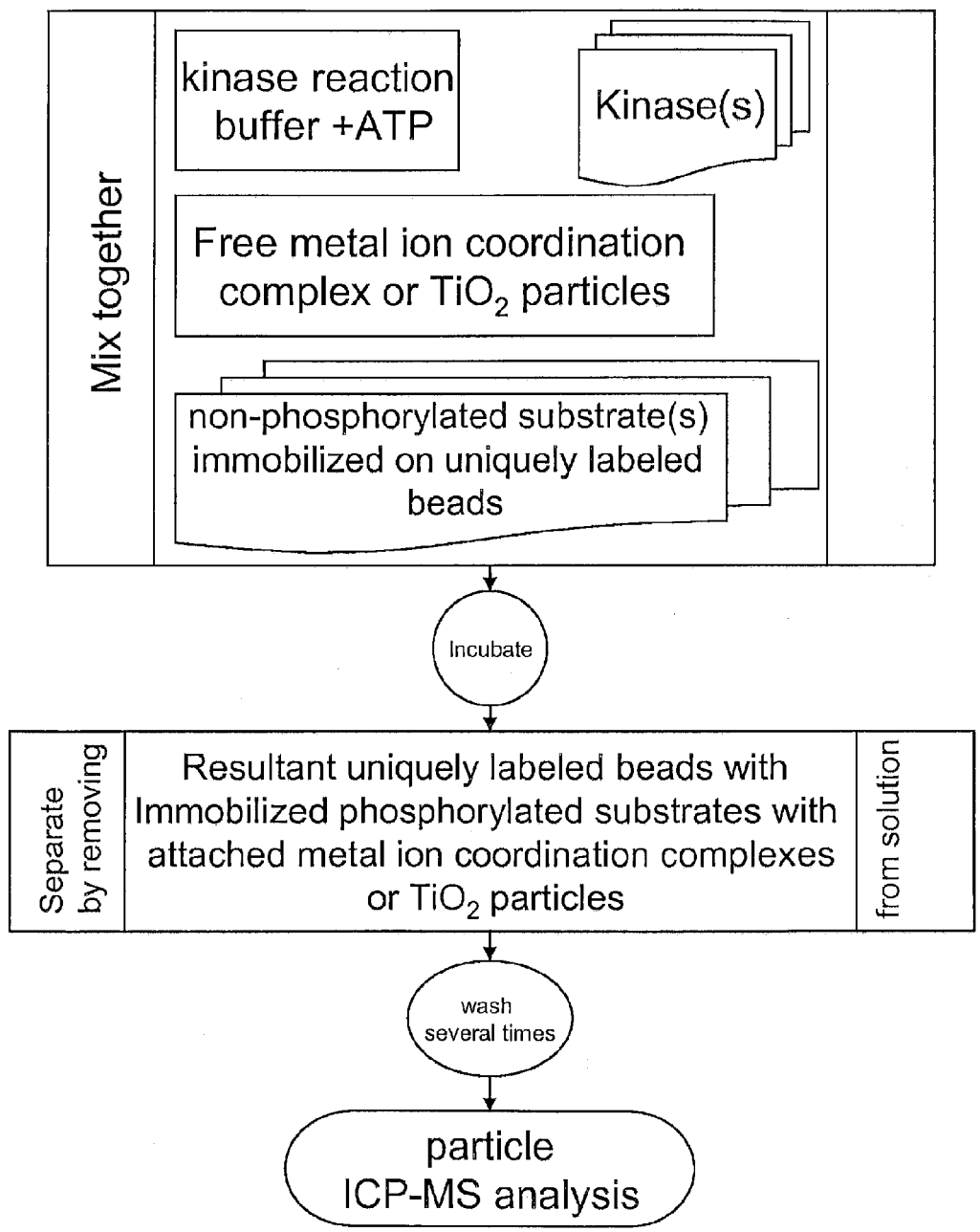
FIG. 7. Flow chart showing method of specific kinase(s) assay using uniquely labeled beads, in accordance with the invention.

Experiment 3. Another embodiment of the invention is related to EGFR kinase activity in human cell lines analyzed by ICP-MS. The adherent A431 cell line was cultured at 70% confluence in alpha-MEM medium (Invitrogen) supplemented with L-glutamine, penicillin-streptomycin, and 10% fetal bovine serum at 37° C. under 5% $CO_2$. Cells were placed on ice and rinsed twice with cold (4° C.) phosphate buffered saline and 400 ul of cell lysis buffer (Cell Signaling #9803) plus phosphatase and protease inhibitors were added to each 100 mm plate. Plate contents were collected by scraping with a plastic cell scraper. The lysate was transferred to a 1.5 ml Eppendorf tube on ice and then clarified at 100,000×g for 15 minutes at 4° C. The suspension grown KG1-a cells were washed with cold buffer by low speed centrifugation (300×g for 10 minutes) and the cell pellet were lysed similar to A431 cells Protein concentration of lysates was determined using the NanoDrop Inc. system. Lysates from the two cell lines were adjusted with lysis buffer to the same protein concentration. KG1-a leukemia cell line does not express EGFR and was used as a negative control for the assay. A431 cells are known to synthesize large amounts of the kinase. The cell lysates were mixed with kinase buffer (Cell Signaling Tech. #9803), 200 mM ATP and agarose-substrate slurry PTP1B (Tyr66) (SignalScout EGFR-substrate on agarose, Stratagene #206307). For positive control, triplicate samples of EGFR-GST kinase (50 ng/sample as described above) were set up instead of the lysate. Negative controls contained the equivalent amount of kinase buffer instead of lysate or kinase. Incubations were carried out at 37° C. for 30 minutes, after which the agarose beads (3 um in diameter according to the manufacturer) were pelleted by low speed centrifugation (500×g, 10 min) and washed 3 times with buffered saline. A 0.0005% suspension of Ti02 particles was added to each sample and incubated for 30 minutes. Thus, the phosphorylated Tyr66 of the PTP1B-agarose substrate interacted with the surface chemistry of Ti02 and bound the titanium particles to the agarose beads. Schematic representation of this process is given in FIG. 4 and a general work flow chart is shown in FIG. 7. Further washing of agarose beads ensures that only specifically bound titanium particles remain in the samples. Finally, pelleted material was dissolved in concentrated HCl, mixed with an equal amount of 1 ppb 1 r internal standard and analyzed by solution ICP-MS. Results are presented in FIG. 3. As evident from the data, only lysates obtained from A431 cells showed a significant response even at the lowest amount of lysate tested (5 ul), while the negative KG1-a cell line did not show EGFR kinase activity at the highest loading. Therefore, the assay may be used to quantify the activity of a known kinase in cellular lysates without the need of using anti-phosphotyrosine antibodies or radioactively labeled reagents.

Experiment 4. In yet a further embodiment, the invention is related to activity of phosphoinositide-3 kinase (P1 3-kinase) and analysis of Akt phosphorylation and utilized culture conditions in which the cells were serum starved, prior to stimulation with a specific growth factor (PDGF). The P1 3-kinase is a lipid kinase, phosphorylating the 3-OH of phosphatidylinositol-4,5-bisphosphate. In vitro substrates for P13K can be L-α-phosphatidyl inositol, L-α-phosphatidylethanolamine, L-α-phosphatidyl-L-serine, L-α-lysophosphatidylcholine and sphingomyelin to name a few. The generation of this signaling lipid by P1 3-kinase is in response to growth factor tyrosine kinase receptor stimulation (for example by PDGF) recruiting P1 3-kinase (consisting of the p85 regulatory domain and the p110 catalytic domain) to the plasma membrane, thereby activating lipid kinase activity. The signaling lipid, phosphatidylinositol-3,4,5-triphosphate (P1P3), recruits kinases that contain pleckstrin homology domains (PH) to the plasma membrane. These include Pdk1, Akt, Tec/Btk tyrosine kinases and Grp1. Pdk1 is a constitutively active kinase whose activity is regulated by localization with target proteins through recruitment to the plasma membrane, or in the case of PKC kinases, through interaction with the P1F binding domain on Pdk1. Pdk1 also activates Akt through phosphonylation. There are a number of targets for Akt, including FKHR, GSK-3, Bad and caspase-9. A role for P1 3-kinase in cancer is suggested by studies that show that the protein levels are increased in some tumors and through identification of a mutation in the PTEN tumor suppressor gene. PTEN is a lipid phosphatase that negatively regulates the amount of P1P3 in the cell. Loss of PTEN function leads to cell proliferation and growth through enhanced stimulation of the downstream targets of the P1 3-kinase pathway. As P1P3 is the direct product of P1 3-kinase, inhibition of this enzyme would similarly reduce the level of P1P3 in the cell and reduce cell growth and proliferation, regardless of the status of PTEN. Inhibitors of P1 3-kinase have been identified, the best known being wortmannin and LY294002 Wortmannin has been shown to be not specific for P1 3-kinase. In a recent study, LY294002 was shown to inhibit one other known kinase (casein kinase II), so it may be more specific than wortmannin.

Cell line and culture. A2780 ovarian cancer cell line is cultured in RPM1 medium (Gibco) supplemented with L-glutamine, insulin (10 ug/ml), and 10% fetal bovine serum at 37° C. under 5% $CO_2$. For kinase stimulation 23-24 hour after initiating serum-starvation, the cells are treated with PDGF BB (R&D Systems #220 BB at 10 ng/ml) or control buffer in serum- and supplement-free media with or without inhibitor (25 uM LY294002) or DMSO for 15 minutes. Once the treatment is concluded, the cells are placed on ice and rinsed twice with cold (4° C.) TBS. Cells are collected by scraping with a plastic cell scraper. The pellet is lysed in cell lysis buffer plus inhibitors (see below). The lysate is transferred to a 1.5 ml Eppendorf tube on ice and then clarified at 100,000×g for 15 minutes at 4° C. Aliquots of cell lysate containing activated kinase of interest is reacted with element-labeled specific substrates attached to a solid support.

In one embodiment, to assay the activity of P13K the synthetic lipid biotinphosphatidylinositol 3,4,5-triphosphate (biotin-Ptd1n (3,4,5)P3) from C39B6 Echelon BioSciences Inc. is reacted with a streptavidin coated 96-well plate (SigmaScreen #M5432) to produce a monolayer of substrate attached to the bottom of the wells to which cell lysates prepared as described above are added. Short incubation for 30 minutes and subsequent washes with Tris buffered saline (TBS) yield Ptd1n (3,4,5)P3 phosphorylated by activated cellular P13K. If cells are incubated with the LY294002 inhibitor prior to PDGF stimulation, then the Ptd1n (3,4,5)P3 is not phosphorylated in the designated wells. Finally, Ti02 in kinase buffer is added to all the wells and after a brief wash concentrated HCl is used to dissolve the biomolecules for solution elemental analysis, for example ICP-MS, to determine the absolute amount of titanium.

Experiment 5. In another embodiment, uniquely labeled beads coated with streptavidin are reacted with biotinylted peptide substrates such that each peptide substrate corresponds to one type of labeled bead. For example, Akt substrate with sequence biotin-PRPAATF (SEQ ID NO: 1), GSK-3 substrate with sequence biotin-YRRAAVPPSPSLSRHSSPHQ(pS)EDEEE (SEQ ID NO: 2), PDK1 substrate with biotinKTFOGTPEYLAPEVR-RE-PRILSEEEQEMFRDFDYIADW (SEQ ID NO: 3), and PKC substrate with sequence biotin-QKRPSQRSKYL (SEQ ID NO: 4) (JPT Peptide Technologies GmbH) can be used for the A2780 stimulated cell system. These labeled beads with peptide substrates in kinase buffer are incubated with cell lysates obtained as described above. After washing by low speed centrifugation (10,000 rpm 10 mm in microcentrifuge), the beads are treated with 0.0005% solution of Ti02 particles. The titanium particles bind to phosphate groups which are attached to the peptides by specific kinases present in the cell lysate. The reaction mixture with beads is once again washed by low speed centrifugation and the beads are analysed by elemental analysis particle analysis in the flow cytometric mode. Beads that carry signals of the unique elemental bead identifier together with the titanium particles indicate that the kinase of interest is present and active in the cell. If inhibitors for a specific kinase are used (LY294002 for Akt for example) during cell cultivation then there will be no concomitant Ti present for the uniquely labeled bead with the Akt substrate attached.

Experiment 6. In yet another embodiment cells grown in culture are exposed to non-phosphorylated element-labeled peptides (Akt and PKA substrates, for example) conjugated with a PTD (protein transfer domain) sequence which enables the peptides to be taken up into the cytoplasm of live cells. Otherwise the element-labeled kinase substrates can be microinjected into the cells, encapsulated into lipid microsomes which are taken up by the cells or transferred into the live cells by other means known in the art. The cells are then stimulated with a specific ligand, PDGF in the example above, fixed and permeabilized in order for antibodies labeled with a different element to gain access to the phosphorylated labeled substrates in the cells. For example, an antibody or other affinity product labeled with Eu (europium) against phospho(Thr)Akt substrate (PerkinElmer AD0184) together with an antibody/affinity product to phospho(Thr)PKA substrate labeled with Sm (samarium) can be used. Single cell particle analysis by the flow elemental analysis (for example, flow-ICP-MS) instrument quantitatively detects levels of kinase activity in each cell according to their elemental signals.

Experiment 7. In yet another embodiment, purified kinases or kinases in cell lysates are mixed with kinase substrates labeled with elemental tags in kinase reaction buffer. This is followed by the addition of beads with Ga3+ ions exposed on the bead surface or with titanium oxide beads that are known to bind specifically phosphate groups. Washing in buffers and low speed centrifugation will yield beads that have captured phosphorylated peptides of kinases that were active towards certain substrates. Single particle analysis by flow ICP-MS gives quantitative results of the kinase reaction.

Cell Lysis buffer (example): 20 mM Tris, pH 7.5, 150 mM NaCl, 1.0% NP40(v/v), 0.5% NaDOC, 0.1 mM MgCl2, 0.2 mM AEBSF, 1.5 microg/ml Aprotinin, 1.0 microg/ml Leupeptin, 2.0 microM Pepstatin, 50 mM NaF, 1.0 mM Na3VO4.

Experiment 8. Normal phosphatase function is essential for maintaining cellular homeostasis. Dysfunction lies at the basis of numerous diseases including tumorigenesis, thereby making phosphatases potential targets for therapeutic drugs. For example, the protein and lipid phosphatase PTEN has been associated with cancer. It is a tumor suppressor and its loss permits constitutive signaling through the P13K pathway and this may lead to the development of a tumor. In cells with low PTEN, there are elevated levels of Ptd1n(3,4,5)P3 which acts as a second messenger to promote oncogenesis. PTEN hydrolyzes phosphate at the 3 position on the inositol ring of Ptd1n(3,4,5)P3 and Ins(1,3,4,5)P4, however the highest catalytic activity in vitro has been observed with the negatively charged, multiply phosphorylated polymer of (Glu-Tyr)n.

Figure 6:
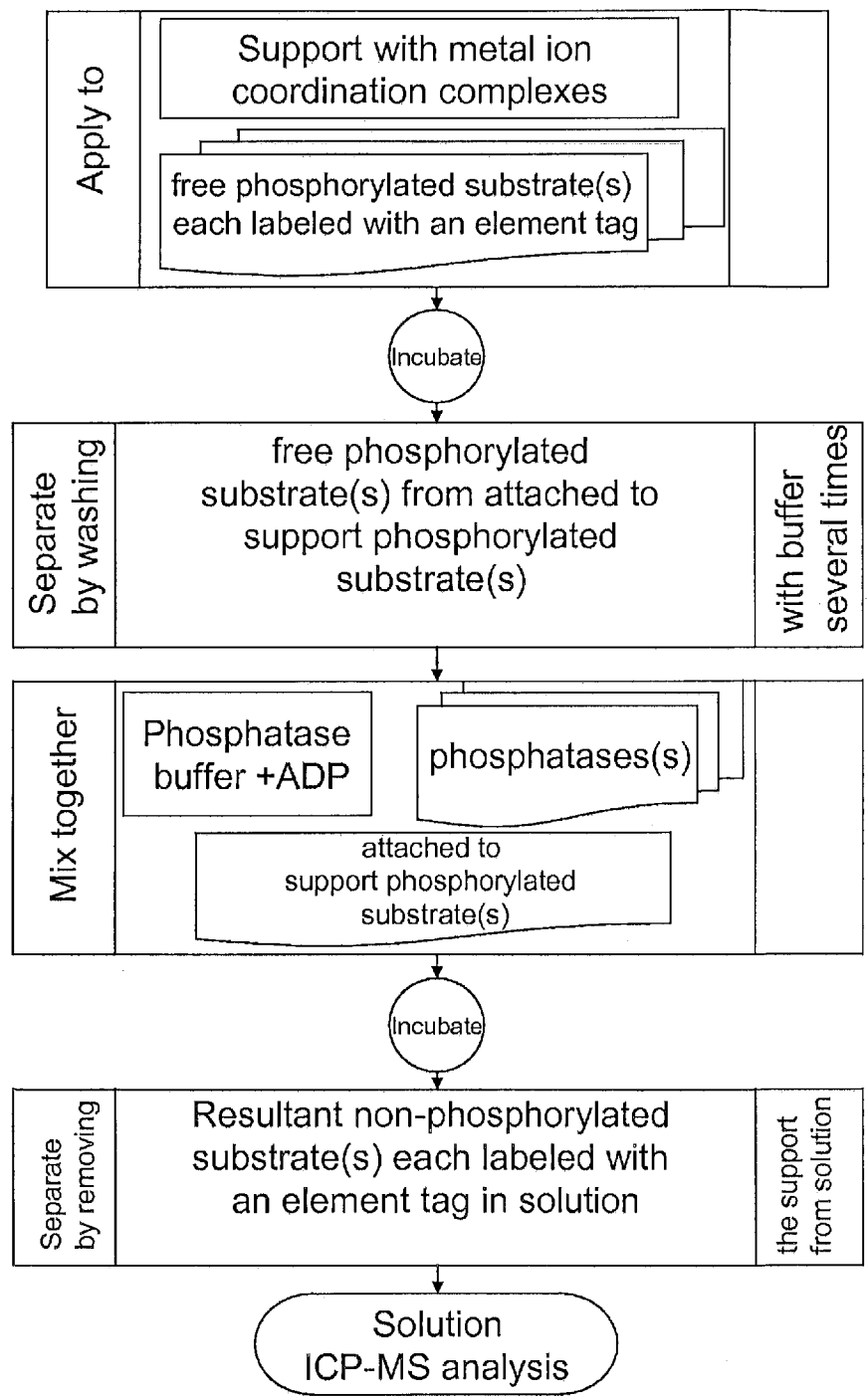
FIG. 6. Flow chart showing method of specific phosphatase(s) assay, in accordance with the invention.
Figure 8:
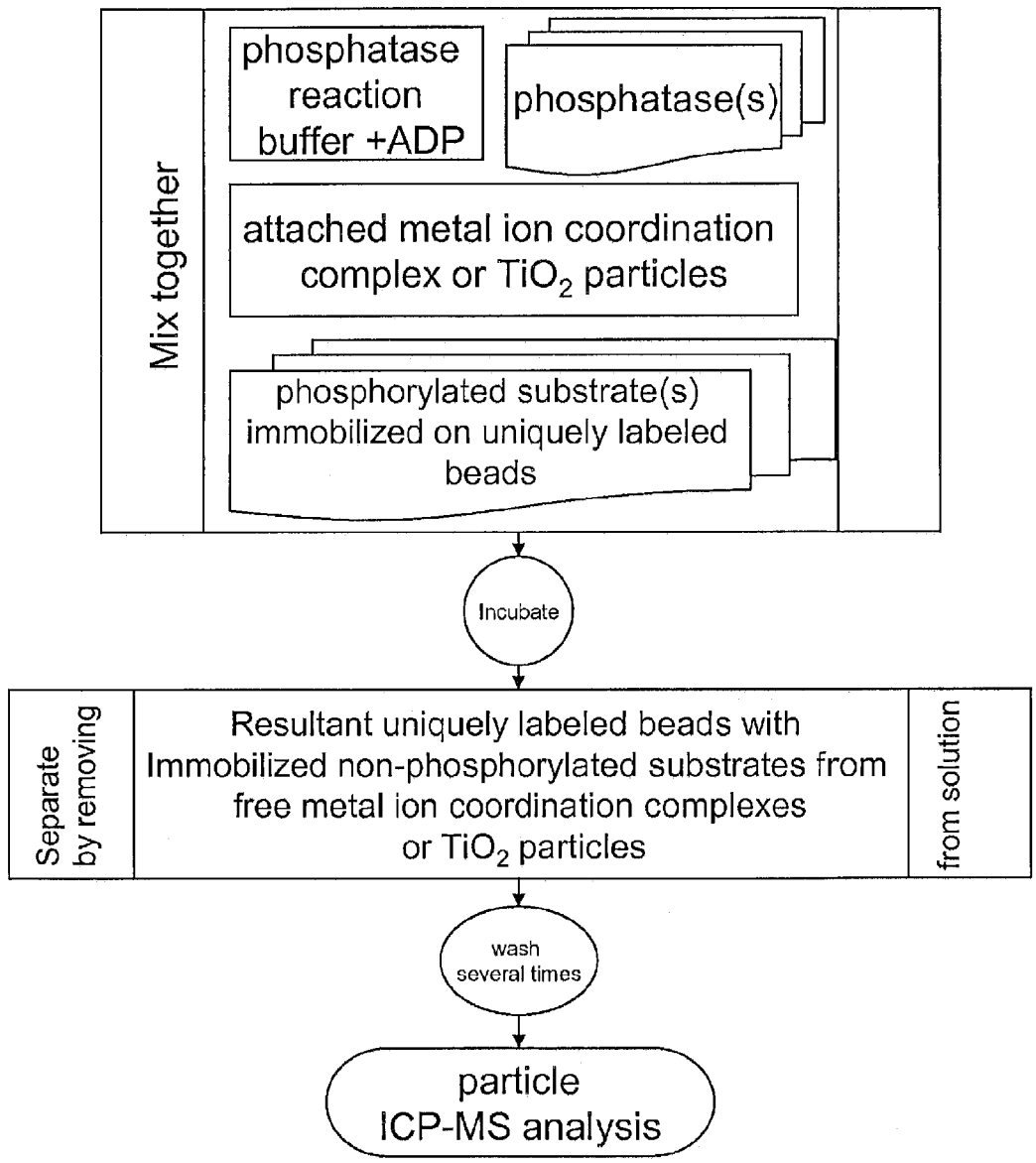
FIG. 8. Flow chart showing method of specific phosphatase(s) assay using uniquely labeled beads, in accordance with the invention.

Protein phosphatases can be studied as purified enzymes or in the context of cell lysates. However, the cell lysis buffer in this case should not contain phosphatase inhibitors such as sodium vanadate or sodium fluoride. An excellent substrate for the mammalian PIP-1B phosphatase is the peptide from an autophosphorylation site (tyr-992) of the epidermal growth factor receptor (EGFR)-Asp-Ala-Asp-Glu-pTyr-Leu-Ile-Pro-Gln-Gln-Gly (SEQ ID NO: 5) (Biomol Inc., #P323-0001). In a solid support experiment, the PIP-i B phosphorylated substrate is immobilized on a surface (microtiter plate or polystyrene bead) and reacted with the phosphatase (purified or as a cell lysate) in a phosphatase reaction buffer. Following washes, $Ga^{3+}$ coordination complex is added to the wells (see flow chart FIG. 6); high phosphatase activity will be detected as a low signal for Ga3+ ions, whereas low phosphatase activity will have a strong Ga signal. Embodiments when phosphorylated substrates are attached to uniquely elemental labeled beads reacted with the specific mix of phosphatases and hO2 particles are also envisaged (included in flow chart FIG. 8).

Experiment 9. Another embodiment is a. method for a phosphatase assay, comprising: incubating ADP and at least one phosphatase, with an immobilized phosphorylated substrate with attached metal ion coordination complex in conditions that enable the phosphatase to dephosphotylate the substrate; separating the free metal ion coordination complex from the immobilized non-phosphorylated substrate and the immobilized phosphorylated substrate with attached metal ion coordination complex; eluting the metal ion coordination complex into a solution; and measuring the solution by elemental analysis.

Experiment 10. Another embodiment is a method for a phosphatase assay, comprising: incubating ADP, at least one phosphatase, and a multitude of phosphorylated substrates with attached metal ion coordination complex immobilized to element labeled supports in such manner that a single type of phosphorylated substrate is attached to a single type of element labeled support in conditions that enable the phosphatase to dephosphorylate the phosphorylated substrates; separating the free metal ion coordination complex from the multitude of non-phosphorylated substrates immobilized to element labeled supports and the multitude of immobilized phosphorylated substrate; and measuring the metal ion coordination complex attached to said residual multitude of phosphorylated substrate immobilized to uniquely labeled supports by elemental analysis. This allows the measurement of the bead's elemental signal. For example, less signals from the metal coordination complex than prior to phosphatase addition will indicate the level of enzyme activity.

Kits

Also provided are kits comprising components to practice the methods of the invention.

A kit is provided for the detection and measurement of elements in a sample, where the measured elements include an element tag attached to a nonphosphorylated substrate and a metal ion coordination complex, comprising: an element tag for directly tagging non-phosphorylated substrate; non-phosphorylated substrate; a solid support; metal ion coordination complex; and optionally, kinase; kinase buffer; and ATP. The kit can further comprise instructions for i) directly tagging the nonphosphorylated substrate with an element tag; ii) incubating kinase with element labeled non-phosphorylated substrate in kinase buffer, iii) attaching metal ion coordination complex to the support; iv) addition of said mixture to support with attached metal ion coordination complex vi) separating bound substrate from unbound substrate; vii) eluting the bound substrate, and viii) detecting and measuring the bound substrate by elemental analysis. The kit can further comprise a non-phosphorylated substrate, wherein the non-phosphorylated substrate is directly labeled with an element tag. The kit can further comprise a multitude of non-phosphorylated substrates directly labeled with unique element tags. The support with attached metal ion coordination complex can be a titanium oxide bead. The kit can further comprise a support with an attached metal ion coordination complex.

Also provided, is a kit for the detection and measurement of elements in a sample, where the measured elements include element labels of uniquely labeled beads and an element of a metal ion coordination complex, comprising: a multitude of non-phosphorylated substrates; uniquely labeled beads; metal ion coordination complex; and optionally, kinase buffer; and ATP. The kit can further comprise instructions for i) immobilizing the non-phosphorylated substrates on element labeled beads in separate solutions; ii) incubating kinase in kinase buffer with the multitude of non-phosphorylated substrates immobilized on uniquely labeled beads, iii) incubating the metal ion coordination complex with the multitude of phosphorylated substrates immobilized on uniquely labeled beads, iv) washing and separating bound substrate from unbound substrate; v) measuring the metal ion coordination complex bound to the multitude of phosphorylated substrate immobilized on uniquely labeled beads by elemental analysis. The kit can further comprise a multitude of non-phosphorylated substrates immobilized on uniquely labeled beads.

Also provided is a kit for the detection and measurement of elements in a sample, where the measured elements include element tags attached to affinity products that recognize phosphorylated substrates, comprising: non-phosphorylated substrate ready to be introduced into a cell; and an element tag for directly tagging the affinity product. The kit can further comprise instructions for i) introducing the non-phosphorylated substrate into a cell; ii) directly tagging affinity products that recognize phosphorylated substrates; iii) fixing and permeabilizing the cells; iv) combining the labeled affinity product with the cells; v) separating bound affinity product from unbound affinity product and vi) detecting and measuring the amount of the bound affinity product labeled with an element tag by particle elemental analysis. The kit can further comprise a multitude of non-phosphorylated substrates to be introduced into a cell. The non-phosphorylated substrate with or without an element tag can be in a sterile solution at a concentration compatible with microinjection into the cell. The kit can further comprise an antibody or affinity product that recognizes phosphorylated substrates, wherein the antibody or affinity product is directly labeled with an element tag. There are many antibodies or affinity products. The kit can further comprise an expression plasmid and wherein the non-phosphorylated substrate is produced by an expression plasmid transfected or electroporated into the cell. The non-phosphorylated substrate with or without an element tag can be in a liposome solution. The affinity product that recognizes the phosphorylated substrates can be selected from a group consisting of antibody, Fab', aptamer, antigen, hormone, growth factor, receptor, protein, peptide, SH2 peptide, and nucleic acid.

Also provided is a kit for the detection and measurement of elements in a sample, where the measured elements include an element tag attached to a phosphorylated substrate and a metal ion coordination complex, comprising: an element tag for directly tagging phosphorylated substrate; phosphorylated substrate; a solid support; metal ion coordination complex; optionally, phosphatase; phosphatase buffer and ADP. The kit can further comprise instructions for i) direct tagging of the phosphorylated substrate with an element tag; ii) attaching the metal ion coordination complex to the support; iii) incubating the element labeled phosphorylated substrate with the support with attached metal ion coordination complex; iv); washing of the support; v) incubating the phosphatase in phosphatase buffer with the support with the attached metal ion coordination complex; vi) separating bound substrate from unbound substrate; ix) eluting the bound substrate, and x) measuring the bound substrate by solution elemental analysis. The support with attached metal ion coordination complex can be a titanium oxide bead. The kit can further comprise a support with attached metal ion coordination complex. The kit can further comprise a phosphorylated substrate which can be directly labeled with an element tag. The kit can further comprise a multitude of phosphorylated substrates directly labeled with unique element tags. Finally, the kit can comprise instructions for the solution to be analyzed by solution elemental analysis.

Also provided is a kit for the detection and measurement of elements in a sample, where the measured elements include an element tag attached to a phosphorylated substrate, an element of a metal ion coordination complex, and elements of uniquely labeled beads, comprising: an element tag for directly tagging phosphorylated substrate; a multitude of phosphorylated substrates; uniquely labeled beads; metal ion coordination complex; optionally, phosphatase; phosphatase buffer and ADP. The kit can further comprise instructions for i) direct tagging the phosphorylated substrates with an element tag; ii) attaching a metal ion coordination complex to the uniquely labeled bead; iii) adding element labeled phosphorylated substrates to the uniquely labeled bead with attached metal ion coordination complex in separate volumes, iv) incubating the substrates; v) washing the beads; vi) combining the multitude of uniquely labeled beads having attached thereto the multitude of resultant phosphorylated substrate labeled with an element tag through coordination to the metal ion coordination complex that is attached to the beads; vii) incubating the phosphatase, the phosphatase buffer and the beads; viii) separating bound substrate from unbound substrate; x) measuring the phosphorylated substrate labeled with an element tag coordinated to the metal ion coordination complex attached to said multitude of uniquely labeled beads by particle elemental analysis. The kit can further comprise a multitude of phosphorylated substrates directly labeled with the same element tag or unique element tags. The kit can further comprise a multitude of uniquely labeled beads with attached metal ion coordination complex. The nonphosphorylated substrate with or without an element tag can be attached to a protein transfer domain (PTD) in a sterile solution. The kit can comprise instructions for a cell lysate to be incubated wherein the cell lysate comprises a phosphatase.

In the kits described above the element can be measured using a mass spectrometer. The element can be an isotope or ion. The element can be selected from a group consisting of the noble and transition metals, lanthanides, rare earth elements, gold, silver, platinum, rhodium, iridium and palladium. The element can include more than one atom of an isotope. The kits can further comprise standards, a dilution buffer, an elution buffer, a wash buffer and/or an assay buffer. Instructions for particle elemental analysis can also be included.

The kits can also include the following reagents:
(i) Protein kinase substrate labeled with element tag
(ii) Lipid kinase substrate labeled with element tag
(iii) Uniquely labeled beads with attached metal ion coordination complex
(iv) Uniquely labeled beads attached to kinase substrate
(v) Uniquely labeled beads attached to phosphatase substrate
(vi) Protein phosphatase substrate labeled with element tag
(vii) Lipid phosphatase substrate labeled with element While the Applicant's teachings are described in conjunction with various embodiments, it is not intended that the Applicant's teachings be limited to such embodiments. On the contrary, the Applicant's teachings encompass various alternatives, modifications, and equivalents, as will be appreciated by those of skill in the art.

All references cited in the disclosure are herein incorporated by reference.

REFERENCE LIST

1. Noland, B. Determining phosphorylating activity of enzyme, by combining enzyme with phosphorylatable compound labeled with acceptor fluorophore, ATP analog, and donor fluorophore, and measuring fluorescence resonance energy transfer. STRUCTURAL GENOMIX INC and Noland, B. [WO2004059291-A2; US20041 46961-A1; AU2003300363-A1].
2. Xue, Q.; Gibbons, I. Multiplexed enzyme assay comprises performing enzyme reactions in presence of substrates to convert substrate to product, separating them, detecting their separation characteristic and determining amount of product.
3. Saxinger, C. Automated peptide synthesis—using novel solvent resistant substrates and novel solns. for storing protected carboxyl terminal aminoacid(s). US DEPT HEALTH & HUMAN SERVICE, US SEC OF COMMERCE, and US NAT INST OF HEALTH. [US7398458-N; WO9102714-A; AU9061 859-A; US6031 074-A].
4. Crouch, S. P. M.; Slater, K. J. Measuring protein kinase activity, involves adding substrate to a solution with ATP and kinase, and another solution with ATP alone, and measuring ATP and/or ADP concentration using a bioluminescence reaction.
5. Hackel, P. O.; Zwick, E.; Prenzel, N.; Ullrich, A. Epidermal growth factor receptors: critical mediators of multiple receptor pathways *Current Opinion in Cell Biology* 1999, 11, 184-89.
6. Cooper, J. A.; Howell, B. The When and How of Src Regulation *Cell* 1993, 73, 1051-54.
7. Schlosser, A.; Vanselow, J. T.; Kramer, A. Mapping of phosphorylation sites by a multi-protease approach with specific phosphopeptide enrichment and nanoLC-MS/MS analysis *Analytical Chemistry* 2005, 77, 5243-50.
8. Meyer, T. J.; Meyer, G. J.; Pfennig, B. W.; Schoonover, J. R.; Timpson, C. J.; Wall, J. F.; Kobusch, C.; Chen, X. H.; Peek, B. M.; Wall, C. G.; Ou, W.; Erickson, B. W.; Bignozzi, C. A. Molecular-Level Electron-Transfer and Excited-State Assemblies on Surfaces of Metal-Oxides and Glass *Inorganic*

What is claimed is:

1. A method to assay kinase activity, the method comprising:
   (a) introducing non-phosphorylated substrates with element tags into live cells;
   (b) incubating the cells having the introduced non-phosphorylated substrates with an agonist or an antagonist of kinase activity;
   (c) fixing and permeabilizing the cells;
   (d) incubating the cells with element-labeled antibodies directed against phosphorylated kinase substrates;
   (e) separating the cells from unbound antibodies; and
   (f) determining an effect of the agonist or the antagonist on cell kinase activity or specificity by measuring the phosphorylated substrates with element tags and attached element-labeled antibodies by using elemental analysis to detect the element tag associated with the phosphorylated substrate.

2. The method of claim 1 wherein step (f) comprises measuring the phosphorylated substrates with element tags and attached element-labeled antibodies by using inductively coupled plasma mass spectrometry to detect the element tag associated with the phosphorylated substrate.

3. The method of claim 1 wherein the step of introducing non-phosphorylated substrates comprises at least one of microinjection, transfection of peptide expressing plasmid, liposome delivery, and incubation with PTD-conjugated substrate.

4. The method of claim 1 wherein the step of separating the cells from the unbound antibodies comprises at least one of low speed centrifugation and filtration.

5. The method of claim 1 wherein the non-phosphorylated substrates are labeled with different element tags, specific to each substrate.

6. The method of claim 1 wherein the non-phosphorylated substrates are labeled with the same element tag.

7. The method of claim 2, wherein the inductively coupled plasma mass spectrometry instrument performs single cell particle analysis to quantitatively detect levels of kinase activity in each cell according to elemental signals detected from each cell.

* * * * *